(12) United States Patent
Billoet

(10) Patent No.: US 9,993,431 B2
(45) Date of Patent: Jun. 12, 2018

(54) DIVERSION-RESISTANT MICROGRANULES AND MICROTABLETS

(75) Inventor: Vincent Billoet, Sotteville les Rouen (FR)

(73) Assignee: Ethypharm, Saint-Cloud (FR)

( * ) Notice: Subject to any disclaimer, the term of this patent is extended or adjusted under 35 U.S.C. 154(b) by 720 days.

(21) Appl. No.: 13/702,787

(22) PCT Filed: Jun. 7, 2011

(86) PCT No.: PCT/EP2011/059410
§ 371 (c)(1),
(2), (4) Date: Feb. 4, 2013

(87) PCT Pub. No.: WO2011/154414
PCT Pub. Date: Dec. 15, 2011

(65) Prior Publication Data
US 2013/0129825 A1 May 23, 2013

(30) Foreign Application Priority Data

Jun. 7, 2010 (FR) ..................... 10 54465
Jul. 20, 2010 (FR) ..................... 10 55921

(51) Int. Cl.
| | | |
|---|---|---|
| *A61K 31/00* | (2006.01) | |
| *A61K 9/20* | (2006.01) | |
| *A61K 9/50* | (2006.01) | |
| *A61K 9/48* | (2006.01) | |

(52) U.S. Cl.
CPC .......... *A61K 9/2022* (2013.01); *A61K 9/2009* (2013.01); *A61K 9/5078* (2013.01); *A61K 9/5084* (2013.01); *A61K 31/00* (2013.01); *A61K 9/2077* (2013.01); *A61K 9/4808* (2013.01)

(58) Field of Classification Search
CPC .. A61K 9/2009; A61K 9/2022; A61K 9/2077; A61K 9/4808; A61K 9/5078; A61K 9/5084; A61K 31/00
See application file for complete search history.

(56) References Cited

U.S. PATENT DOCUMENTS

| | | | |
|---|---|---|---|
| 6,908,626 B2 * | 6/2005 | Cooper | ............... A61K 9/5084 424/451 |
| 2003/0068371 A1 | 4/2003 | Oshlack | |
| 2007/0224129 A1 | 9/2007 | Guimberteau | |
| 2008/0193540 A1 | 8/2008 | Soula | |
| 2009/0041838 A1 * | 2/2009 | Guimberteau | ....... A61K 9/5047 424/452 |
| 2010/0266701 A1 | 10/2010 | Guimberteau | |

FOREIGN PATENT DOCUMENTS

| | | | |
|---|---|---|---|
| FR | 2 881 652 | | 8/2006 |
| FR | 2 892 937 | | 5/2007 |
| WO | WO 97/12605 | * | 4/1997 |
| WO | WO 2006/056712 | | 6/2006 |

* cited by examiner

*Primary Examiner* — Ali Soroush
(74) *Attorney, Agent, or Firm* — Dinsmore & Shohl LLP

(57) ABSTRACT

The invention relates to the use of an oral dosage form based on microgranules and/or microtablets to reduce the abusive use of at least one active principle contained therein. The aim of the invention is to prevent the diversion of an oral dosage form based on microgranules and/or microtablets containing at least one active principle capable of causing a dependency, a gelling agent, and a gelling activator. The gelling agent and the activator are only brought into contact with each other in the event of diversion by crushing. Said judiciously selected pair of excipients confers a viscosity to the formulation, such that said formulation cannot be administered by injection or does not release the active principle rapidly by forming a gel when it comes into contact with the mucous membrane if nasally administered.

15 Claims, 1 Drawing Sheet

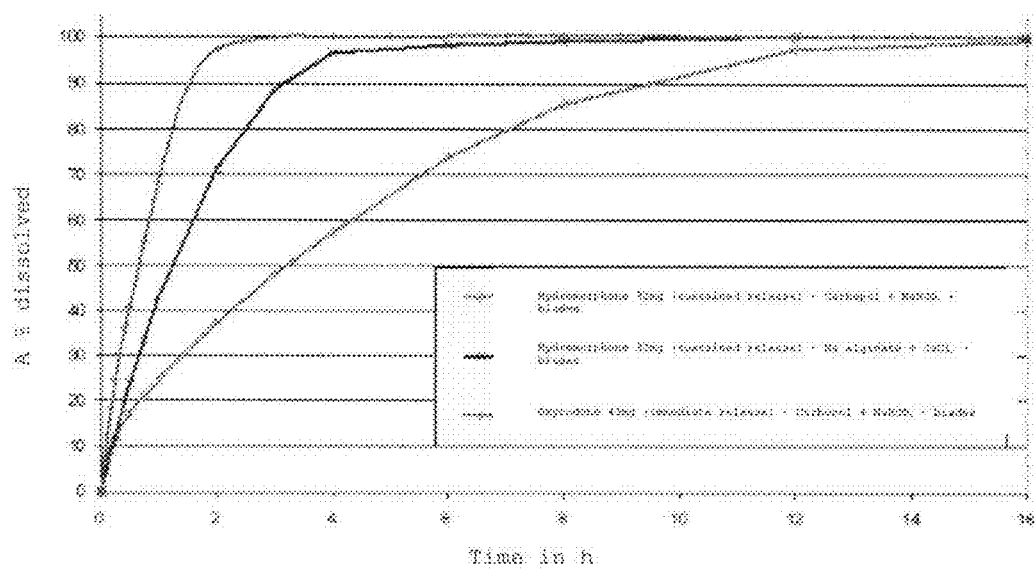

DIVERSION-RESISTANT MICROGRANULES AND MICROTABLETS

The invention relates to the use of an oral dosage form based on microgranules and/or microtablets to reduce the abusive use of at least one active principle contained therein.

The active principles considered are pharmaceutical active principles, for example those classed in the category of narcotic substances which can thus provoke dependency in humans. Said active principles are those which can give rise to improper use. More particularly, the active principles considered are analgesic active principles.

The abusive use of a solid dosage form for oral usage is encountered in the case of addictive behaviour, for example in drug addicts.

It is known that in general the effect, producing the dependency is more important in the case of parenteral or nasal administration than in the case of oral administration. Persons seeking to divert the use of a solid oral dosage form containing at least one active principle creating a dependency are generally going to try either to reduce said solid dosage form into the state of a dusting powder that can be inhaled or swallowed, or to extract the active principle in a solvent, for example water, so as to be able to inject it using a syringe.

Obtaining an injectable liquid form from a solid oral dosage fonts goes through a step of aqueous or organic extraction of the targeted active principle. Said extraction is generally preceded by grinding.

Inhalation or injection are generally used by drug addicts because these are methods of abuse that make it possible to accentuate the sought after effects of the active principle due to a faster absorption in the body than in the case of oral administration.

There thus exists a problem of public health linked to the misuse of drugs, and in particular solid oral drugs, and more especially in the case of analgesic active principles.

The aim targeted by the present invention is to prevent the abuse of an oral dosage form based on microgranules and/or microtablets containing at least one active principle that could create a dependency, a gelling agent and a gelling activator. The gelling agent and the activator are only brought into contact in the case of diversion by crushing. Said judiciously selected pair of excipients confers to the formulation a viscosity such that said formulation cannot be administered by injection or does not release the active principle rapidly by forming a gel when it comes into contact with the mucous membrane in the case of administration by nasal route.

The prior art describes several attempts as responses to the abuse of a drug and in particular drugs containing an opioid.

The patent FR2361914 describes tablets of Propiram containing derivatives of methyl cellulose, substances that swell in water, to prevent the extraction by water of the active principle. The crushing of such tablets enables an easy extraction of the active principle.

The application PCT WO2008150526 describes an oral dosage form containing a gelling agent, a lipid and an active substance.

The gelling agent may be hyaluronic acid, carboxymethylcellulose, guar gum or a combination of guar gum and xanthan gum.

The lipid may be an animal, vegetable or mineral oil, liquid or solid.

In the presence of water, a viscous gel forms so as to prevent the extraction of the active substance.

The application PCT WO2006056712 describes a dosage form containing a caking agent, a viscosifier agent and beads insoluble in aqueous or aqueous-alcoholic media, incompressible and inert.

The caking agent may be an oil or a wax.

The viscosifier agent may be a polyacrylic acid, a polyalkylene glycol, a polyvinylpyrrolidone, a gelatine, a polysaccharide, such as sodium alginate, pectins, guars, xanthans, carrageenans, gellans and derivatives of cellulose (e.g. hydroxypropylmethylcellulose, methylcellulose, hydroxyethylcellulose, carboxymethylcellulose), and mixtures thereof.

The solutions provided by the documents of the prior art are based on the use of a gelling agent substance in the presence or not of a hydrophobic substance to reduce the extraction of the active principle.

However, these solutions are not completely satisfactory because the increase in the viscosity of the ground material of the solid dosage forms and thus the capacity to recover or not the active principle uniquely depends on the intrinsic viscosifier properties of gelling agents and their quantity in the formulation.

An essential objective of the present invention is to propose a dosage form comprising an active principle, the abusive use of which by crushing then injection or inhalation is not possible.

This objective is attained by an oral dosage form based on two populations of microgranules or microtablets of identical external appearance, the first population (1) containing at least one gelling agent and at least one active principle that could create a dependency and the second population (2), without active principle and gelling agent, containing a gelling activator.

It may further be envisaged that the first-population of microgranules or microtablets contains at least one gelling activator and at least one active principle and that the second population of microgranules or microtablets without active principle and gelling activator contains a gelling agent.

Achieving a gelling reducing the possibility of diversion of use is obtained not by increasing the quantity of gelling agent in the formulation, as described for example in the prior art, but by optimising the use of the viscosifier properties of a gel.

When the dosage form of the invention releases said microgranules and/or microtablets into the body, in particular into the gastric juice, the populations (1) and (2) are not in contact. There is thus no gelling of the dosage form. The population (1) is released in the body like a fully separate dosage form: it may thus be formulated like any pharmaceutical formulation known to those skilled in the art with immediate or sustained release.

It is known from the prior art that the addition of a gelling agent can modify the sustained release of a dosage form.

Unlike the prior art, the nature of the gelling agent and the quantity of the gelling agent do not modify the release profile of the active principle of the population (1) released into the body.

Definitions in the sense of the present description of the invention:

Dosage Form

"Oral dosage form." is taken to mean any oral dosage form capable of being prepared from microgranules and/or microtablets comprising the active principle, particularly a suspension, a syrup, a tablet, a capsule.

Neutral Support

"Neutral support" or "neutral core" or even more simply "neutral" are intended to mean inert spherical or quasispherical supports of size comprised between 50 μm and 3 mm and preferentially between 100 and 1000 μm, such as those normally used in the pharmaceutical industry as base supports for active principles for the constitution of microgranules for example.

Microgranules

The microgranules of the present invention relate to spherical dosage units, constituted in their centre of a neutral support, covered with at least one layer.

The microgranules of the present invention may also be obtained by a method known in itself such as, for example, extrusion-spheronisation, wet or hot granulation.

Microtablets

The microtablets of the present invention relate to dosage unit resulting front the compression of powders or granules and have a size less than 10 mm.

Sustained Release

In the present application, the term sustained release will be used to designate a release profile of the active principle that is modified compared to that which the active principle would have had alone in an immediate release system as defined, by the European Pharmacopoeia (quantity of active principle released in 45 minutes at least equal to 75%, Ph. Eur., 6th edition 2.9.3.)

Gelling Activator

In the present application, the term "gelling activator" will be used to designate a compound capable of increasing the gelling power of a given gelling agent. For example, the following gelling activators could be used: a ionic agent, such as polyvalent cations, generally bi- or trivalent, such as the calcium ion or the aluminium ion which attach themselves to certain precise sites of macromolecular chains, which are called fixation sites or cross-linking sites, thereby forming bridges between said chains. The gels thereby formed are sometimes known as "ionotropic gels". Among these gels may be cited alginates, pectins, carrageenans, carboxymethylcellulose and chitosans.

In the case of alginate, for example, the polyvalent cations, such as the calcium $Ca^{2+}$ ion, form bridges at certain precise sites of the polysaccharide chains, corresponding to polyglucuronic sequences, thereby forming a gel.

In the present application, the term activator will also be used to designate a pH modifier, for example an organic or inorganic acid or base capable of substantially modifying the pH of a solution/aqueous suspension.

In the present application, the term gelling activator could also be used to designate a compound of mineral origin.

For example, in the case of xanthan gum, the use of a clay derivative, for example Veegum®, is going to increase in a synergic manner the viscosity of the suspension obtained once the mixture is dispersed in water.

DETAILED DESCRIPTION OF THE INVENTION

The invention relates to an oral dosage form based on microgranules and/or microtablets comprising two populations of microgranules or microtablets of identical external appearance, the first population (1) comprising at least one active principle that could, create a dependency and at least one gelling agent, and the second population (2), without active principle and gelling agent, comprising at least one gelling activator.

It may also be envisaged that the first-population (1) of microgranules or microtablets comprise at least one active principle that could create a dependency and at least one gelling activator, and that the second population (2) of microgranules or microtablets, without active principle and gelling activator, comprise at least one gelling agent.

According to a first embodiment of the invention, the oral dosage form consists of two populations of microgranules or two populations of microtablets.

More precisely, the first population of microgranules may comprise a neutral support and at least one mounting layer comprising at least one active principle, and optionally a pharmaceutically acceptable binder agent and a gelling agent present either in the mounting layer or in a separate layer.

The second population of microgranules may comprise a neutral support and at least one mounting layer comprising at least one gelling activator and optionally a pharmaceutically acceptable binder agent.

In the event of abuse of the oral dosage form, for example by crushing of the microgranules in the presence of water or another solvent for example alcohol, the first population of microgranules releases the active principle and the gelling agent and in a concomitant manner and without possible segregation, the second population of microgranules releases the gelling trigger so as to reduce or preferably prevent the solubilisation of the active principle contained in the microgranules.

Optionally, the first population of microgranules comprises a coating based on at least one hydrophobic or water soluble polymer. The hydrophobic polymer prevents the immediate release of the active principle and delays the release (sustained release). The nature and the quantity of gelling agent do not modify the behaviour of the sustained release hydrophobic polymer. The coating layer comprises, optionally, at least one plastifier and optionally at least one surface active agent. According to another embodiment of the invention, the oral dosage form consists of two populations of microgranules. The hydrophobic polymer is present in sufficient quantify to prevent the immediate release of the active principle during normal conditions of use of the oral dosage form according to the invention.

In an advantageous manner, the neutral support is constituted either of sucrose and starch or at least one excipient of hydrophobic nature chosen from: cellulose, derivatives of cellulose (microcrystalline cellulose), derivatives of phosphates (calcium phosphates), silica and silicate derivatives (magnesium silicate, aluminium silicate and mixtures thereof), or instead any type of excipient able to form spheres of regular size, for example tartaric acid.

According to another embodiment of the invention, the oral dosage form comprises microtablets.

The different methods of manufacturing tablets, for example by direct compression or by compression after wet process or dry process granulation, are presented in "Remington's Pharmaceutical Sciences, 16$^{th}$ Ed, 1980, Mack Publ. Co. of Easton, Pa., USA".

The microtablets according to the invention may be prepared by direct compression or by any other appropriate method.

In an advantageous manner, the microtablets according to the present invention are obtained by mixing powder subjected to homogenisation in a dry miser. The mixture is then subjected to a compression force which confers on the resulting tablet a satisfactory hardness enabling the industrialisation of its manufacture and its handling in normal conditions without particular operating precautions.

According to a particular aspect of the invention, the oral dosage form consists of two populations of microtablets of identical external appearance, the first population of microtablets comprising at least one active principle and a gelling agent, and the second population of microtablets, without active principle and gelling agent, comprising at least one gelling activator.

It may also be envisaged that the oral dosage form consists of two populations of microtablets of identical external appearance, the first population of microtablets comprising at least one active principle and a gelling activator, and the second population of microtablets, without active principle and gelling activator, comprising at least one gelling agent.

In the event of abuse of the oral dosage form, for example by crushing of the microtablets in the presence of water or another solvent for example alcohol, the first population of microtablets releases the active principle and the gelling agent and in a concomitant manner and without possible segregation, the second population of microtablets releases the gelling trigger so as to reduce or preferably prevent the solubilisation of the active principle contained in the microtablets.

According to another embodiment of the invention, the oral dosage form consists of two populations of microtablets of identical external, appearance.

The first population of microtablets comprises at least one active principle and a gelling activator.

The second population of microtablets comprises sit least one gelling agent. Each microtablet according to the present invention comprises at least one pharmaceutically acceptable diluent.

Optionally, the first population of microtablets comprises a coating based on at least one hydrophobic polymer. The hydrophobic polymer prevents the immediate release of the active principle. The coating layer comprises, optionally, at least one plastifier and optionally at least one surface active agent. In an advantageous manner, the gelling agent is present in the final dosage form at a rate of 1 to 100 mg, more preferentially from 1 to 50 mg and even more preferentially from 1 to 30 mg.

In an advantageous manner, the gelling activator is present in the final dosage form, at a rate of 1 to 100 mg, more preferentially from 1 to 50 mg and 10 even more preferentially from 1 to 30 mg.

Also in an advantageous manner, a water soluble polymer and a non water soluble polymer may enter into the composition of a coating layer of the micro-granule or the microtablet. Said, water soluble polymer is chosen from the group comprising particularly polyvinylpyrrolidone, hydroxypropylmethyl cellulose and mixtures thereof, and the non water soluble polymer is chosen from the group comprising particularly acrylic and/or methacrylic resins, cellulosic polymers, vinylic polymers and mixtures thereof.

Preferably, the active principle(s) are incorporated in the active layer of the microgranule in association with a pharmaceutically acceptable binder agent, such as those normally used in the pharmaceutical industry for the fixation of active principles on the surface of neutral supports. Thus, the method of fixing the active layer described in the parent EP 1 200 071 may be suitably employed for the fixation of the active layer within the scope of the present invention.

In a preferred manner, the active layer of microgranules according to the invention is applied by spraying a dispersion of active principle in a solvent (known as mounting dispersion). Advantageously, said dispersion also contains the binder agent.

Among pharmaceutically acceptable binder agents, preferentially binder agents of hydrophilic nature are used and particularly derivatives of cellulose such as HPMC, in particular the grades Pharmacoat® 603 and Pharmacoat® 606, derivatives of polyvinylpyrrolidone, in particular the grade PVP K 30 and also derivatives of polyethylene glycol, in particular polyethylene glycol, the molecular weight of which is between 3000 and 7000, such as PEG4000 and PEG6000 particularly, and mixtures thereof.

The solvent, of the sprayed mounting dispersion needs to be adapted to the active principle or to the mixture of active principles employed. For instance, it is possible for example to use water, organic solvents, among them ethanol or aqueous-alcohol solutions of various concentrations for forming the solution or suspension based on the active layer.

A surface active agent may be added to the mounting phase to improve the solubility of the active principle or to stabilise the mounting suspension. The surface active agent is used in quantities from 0 to 50% and preferentially between 0 and 20%. Among the surfactants that may be used, may be cited alkaline or alkaline earth salts of fatty acids (of which stearates, preferably of calcium, magnesium, aluminium or zinc), sodium dodecyl sulphate and sodium docusate being preferred, polyoxyethylenated oils, preferably hydrogenated polyoxyethylenated ricin oil, polyoxyethylene-polyoxypropylene copolymers, polyoxyethylenated esters of sorbitan (=polysorbates), derivatives of polyoxyethylenated ricin oil, stearylfumarates, preferably of sodium, glycerol behenate, benzalkonium chloride, acetyltrimethyl ammonium bromide, cetyl alcohol and mixtures thereof.

In so far as possible, it is preferable to use solvents that are non-toxic and easy to remove by evaporation during drying in order that no trace remains in the microgranules.

In an advantageous manner, the gelling agents are chosen from the following groups of polymers:
  polyacrylic acids and derivatives thereof, of Carbopol® type (known as Carbomer or carboxy polymethylene)
  polyoxyethylenes (POE), and/or
  polyvinyl alcohols (FVA)
  polyvinylpyrrolidones (PVP), and/or
  gelatines, and/or
  derivatives of cellulose (e.g. hydroxypropylmethylcellulose, methylcellulose, hydroxyethylcellulose, carboxymethylcellulose), and/or
  polysaccharides, preferably in the sub-group comprising: alginates, in particular sodium alginate, pectins, guars, xanthans, carrageenans, gellans and—mixtures thereof.

In an advantageous manner, when the gelling activator is an alginate, for example Protanal® 1.20 or 200, the gelling activator is a divalent cation such as the $Ca^{2+}$ ion, the $Ba^{2+}$ ion, the $Zn^{2+}$ ion, the $Cu^{2+}$ ion, the $Mg^{2+}$ ion.

When the gelling agent is Carbopol®, the gelling activator is an alkalising agent such as potassium hydroxide, sodium bicarbonate, sodium hydroxide, sodium phosphate or an organic amine such as triethanolamine.

Generally speaking, the gelling activator used in association with the gelling agent enables the formation of bridges at certain sites of the polymeric chains of the gelling agent or instead enables the reinforcement of the polymeric network.

In an advantageous manner, according to the invention the gelling agent/gelding activator pair is chosen from the following associations;
  carboxy polymethylene (Carbopol®)/sodium bicarbonate,
  alginate/$Ca^{2+}$ ion,
  alginate/a clay derivative, for example Veegum® (magnesium and aluminium silicates),
  xanthan gum/a clay derivative, for example Veegum® (silicates of magnesium and aluminium), polyvinyl alcohols/Cu²⁺ ion,
pectins/Ca²⁺ ion,
carboxymethylcellulose/Al²⁺,
gellan gum/Ca²⁺,
K-carrageenan/K⁺,
l-carrageenan/Ca²⁺.

The different populations of microgranules or microtablets according to the present invention all have the same external appearance, such that the microgranules or the microtablets containing the active principle are physically indiscernible from the microgranules or microtablets comprising the gelling agent or the gelling activator. This with the aim that the separation of the different populations of microgranules or microtablets, with a view to abuse, is rendered impossible.

In an advantageous manner, the coating making it possible to indifferent late the different populations, of microgranules or microtablets is constituted of a polymer film which can be coloured, for example Opadry®.

In an advantageous manner, the coating can make it possible to control the release of the active principle contained in the microgranules or the microtablets. The coating then contains a hydrophobic polymer preventing the immediate release of the active principle in quantity comprised between 50% to 100%, preferably between 50% and 90%, more preferentially between 50% and 80%, 50% and 70%, or 50% and 60%, of the dry mass of said coating layer.

The coating ratio represents the ratio of the quantity of dry mass constituting the coating ensuring a sustained release of the active principle over the total mass of the microgranule or the microtablet before coating (dry mass). The coating ratio is comprised between 0.1% to 50% m/m, preferably, from 2% to 30% m/m, and, ever; more preferentially, from 5% to 30%. Or in other words, the ratio between the mass of dry varnish (=polymer and any additives in the dry mass) constituting the coating preventing the immediate release of the active principle over the total mass of the micro-granule or the microtablet before coating (dry mass) is comprised between 0.1% to 50% m/m, preferably, from 2% to 30% m/m, and, even more preferentially, from 5% to 30%.

The polymers used to ensure a sustained release of the active principle are polymers of hydrophobic nature, preferably, selected from the group of following products: non water soluble derivatives of cellulose, derivatives of (meth) acrylic(co)polymers, vinylic derivatives and mixtures thereof.

More preferentially, the hydrophobic polymer(s) preventing the immediate release of the active principle is (are) selected from the group of following products: ethylcellulose, cellulose acetate butyrate, cellulose acetate, type A and type B ammonio-methacrylate copolymers sold under the trade name Eudragit®, particularly Eudragit® RS 30D, Eudragit EE 30D, Eudragit® RL 30D, Eudragit® RS PO and Eudragit® RL PO of the family of polyethyl acrylate, methyl methacrylate, trimethylamonioethyl methacrylate), polyvinylacetates and mixtures thereof.

A plastifier agent may be added to the coating dispersion at a rate of 0% to 50% m/m, preferably, from 2% to 25% m/m, in dry mass of coating polymer.

The plastifier agent is selected particularly in the group of following products: glycerol and esters thereof, preferably in the following sub-group: medium chain triglycerides, acetyl glycerides, glyceryl-mono-stearate, glyceryl-triacetate, glyceryl-tributyrate, phthalates, preferably in the following sub-group: dibutylphthalate, diethylphthalate, dimethylphthalate, dioctylphthalate, citrates, preferably in the following sub-group: acetyltributylcitrate, acetyltriethylcitrate, tributylcitrate, triethylcitrate, sebacates, preferably in the following sub-group: diethylsebacate, dibutylsebacate, adipates, azelates, benzoates, chlorobutanol, polyethylene glycols, vegetable oils, fumarates, preferably diethylfumarate, malates, preferably diethylmalate, oxalates, preferably diethyloxalate, succinates; preferably dibutylsuccinate, butyrates, esters of cetyl alcohol, malonates, preferably diethylmalonate, ricin oil (this being particularly preferred), and mixtures thereof.

More preferentially, the plastifier agent is selected from the group of following products: acetyl monoglycerides, particularly Myvacet® 9-45, triethylcitrate (TEC), dibutylsebacate, triacetine and mixtures thereof.

The surfactant is optionally present in the coating at a rate of 0 to 30% m/m, preferably from 0 to 20% m/m, and, even more preferentially, from 5 to 15% of the dry mass of plastifier. The surfactant is preferably selected from the group of following products: alkaline or alkaline earth salts of fatty acids (preferably stearates, preferably of calcium, magnesium, aluminium or zinc), sodium dodecyl sulphate and sodium docusate being preferred, polyoxyethylenated oils, preferably hydrogenated polyoxyethylenated ricin oil, polyoxyethylene-polyoxypropylene copolymers, polyoxyethylenated esters of sorbitan (polysorbates), derivatives of polyoxyethylenated ricin oil, stearylfumarates, preferably of sodium, glycerol behenate, benzalkonium chloride, acetyltrimethyl ammonium bromide, cetyl alcohol and mixtures thereof.

An inert filler may be present in the coating at a rate of 0 to 50% m/m, preferably from 0 to 20% m/m, and, even more preferentially, from 5 to 20% of the dry mass of the coating polymer.

The inert filler uniformly distributed in the coating is chosen from the group comprising particularly talc, anhydrous colloidal silica, magnesium stearate, glycerol monostearate and mixtures thereof.

The oral dosage form based on microgranules according to the present invention can come in the form of a sachet or single dose packaging of microgranules or tablets obtained from microgranules, tablet obtained from microgranules, or capsule containing microgranules.

The oral dosage form based on microtablets according to the present invention can come in the form, of a bag or single dose packaging of microtablets or capsule containing microtablets.

The oral dosage form based on microgranules or microtablets according to the present invention comprises microgranules or microtablets either with modified release of the active principle or with immediate release of the active principle.

To prepare the microtablets according to the present invention, excipients known to those skilled in the art are used.

For example, sugars and carbohydrates are commonly used as binders and disintegrants in the formulation of tablets due to their pleasant taste.

Directly compressible lactose is one of the excipients among the most used in direct compression: it is however incompatible with certain active principles.

Directly compressible starch (or pregelatinised starch) undergoes a chemical and mechanical treatment to avoid the aggregation of the grains of starch. It is constituted of 5% amylase, 15% amylopectin and 80% non-modified starch. It is used as a binder (in the form of starch), as a diluent or as a disintegrant.

Directly compressible sucrose contains between 95 and 98% of sucrose and an additive such as starch, maltodextrine, inert sugar or a lubricant. It is used as a binder and above all as a diluent.

Among the other excipients for direct compression are mannitol, microcrystalline cellulose and dicalcium phosphate. Granules for direct compression, having a good fluidity based on fructose, lactitol or xylitol have also been developed, they are prepared by atomisation or by agglomeration.

The dosage units according to the invention may be film coated, either to improve their appearance, or to mask the colour, or to protect the active principle from light, humidity or oxygen in the air.

The Active Principle

Constituting active layer of the microgranules according to the invention comprises at least one pharmaceutical active principle which may be of any nature.

The microgranules or the microtablets according to the present invention may comprise, as active principle, active principles acting on the central nervous system.

The active principles acting on the central nervous system are preferably chosen from anti-epileptics, anti-parkinsonians, psycho-stimulants, psychotropics, antidepressors, anxiolytics and anti-psychotics for example.

The analgesics may be chosen from the non opiates, low opiate analgesics, mixed opioids, morphinics or spasmodics.

Even more precisely, the active principle implemented is chosen from the following compounds: Alfentanil, Alphamethylfentanyl, Buprenorphine, Codeine, Dextropropoxyphene, Dihydrocodeine, Hydrocodone, Hydromorphone, Methadone, Morphine, Oxycodone, Oxymorphone, Sufentanil, and Tramadol, pharmaceutically acceptable salts of said compound and mixtures of said compounds and/or salts thereof.

The Method of Preparing the Microgranules

The microgranules of the present invention may be prepared by the method which comprises the following steps:
—introducing neutral spherical supports into a fluidised bed reaction chamber, —spraying on said neutral spherical supports at least one active principle in solution or in suspension in an organic and/or aqueous solvent to which has been added at least one water soluble or non water soluble polymer, —spraying a coating suspension comprising at least one hydrophobic polymer on the coated particles obtained at the preceding step, —optionally, drying the medicinal microgranules thereby obtained.

Preparations of the Mounting Dispersion

The step known as mounting of the active layer according to the present invention makes it possible to obtain, microgranules, the active principle content of which is both precise and uniform.

The dispersion known as mounting is the dispersion in which the active principle(s) are going to be dissolved or suspended (dispersed) and which are going to be sprayed on the surface of the microgranules. Said dispersion contains advantageously a conventional binder agent, also dissolved.

Mounting of the Active Layer

The active principle is applied on the granules in a conventional manner by spraying, in fluidised bed or in perforated turbine for example. Generally speaking, this method is based on simultaneous spraying through a nozzle, the active principle(s) and optionally a binder, which are dissolved or dispersed in the mounting solution, which guarantees for this step of the method a perfect homogeneity of content.

The time necessary for the mounting is highly variable and depends on the quantity of active principle to be sprayed and its solubility in the mounting solution. Generally speaking it is comprised between 1 and 10 hours.

At the end of the mounting step, the microgranules are dried in fluidised bed or in perforated turbine then screened.

According to a variant of the present invention, the gelling agent layer may be applied either directly on the neutral (granule), or on the active layer after drying of the latter.

Application of the Gelling Activator

The gelling activator is applied, on the neutrals (granules) in a conventional manner by spraying, in fluidised bed or in perforated turbine for example.

Coating of the Microgranules

The coating polymer is applied on the preceding microgranules in a conventional manner by spraying, in fluidised bed or in perforated turbine for example. Generally speaking, this method is based on simultaneous spraying through a nozzle, the coating polymer(s) and optionally a plastifier and/or a surface active agent and/or an inert filler which are dissolved or dispersed in a suitable solvent.

An organic polymer solution may be used for the coating: in this case, the method consists in spraying the solution and drying in the same equipment.

If the vehicle is water, an aqueous dispersion of polymer is used, a plastifier must be added to improve the quality of the coating. The method then consists in spraying the dispersion, drying in the same equipment and, if necessary, a step of maturation of the coating film (also known as curing) which enables a homogeneous and uniform film to be obtained. The curing may be carried cut in fluidised bed, in turbine or in an oven for example.

The time necessary for the coating is highly variable and depends on the quantity of polymer to be sprayed. Generally speaking it is comprised between 1 and 10 hours.

At the end of the coating step, the microgranules are dried in fluidised bed then screened.

The following examples are given by way of illustration of the present invention. They do not constitute in any case a limit of the possibilities.

EXAMPLES

Example 1a: Sustained Release Usage
Diversion-Resistant Microgranules of Morphine Sulphate a) Preparation of the population 1, including the active principle and the gelling agent.

The active principle used is morphine sulphate.

The neutral cores used are sugar spheres (Neutrals #30 NPPHARM). The size of said supports is of the order of 400 to 600 μm.

The gelling agent used is a derivative of polyacrylic acids, type Carbopol® 971 or 974.

The binder agent used is hydroxypropylmethylcellulose 603 (HPMC 603).

The Carbopol® is solubilised in water, then the HPMC 603 and finally the morphine sulphate are added to said aqueous solution, constituting the mounting solution. The mounting solution is sprayed in fluidised bad (Glatt), as is the coating suspension conferring the properties of sustained release to said population of microgranules.

Formulas of the different populations 1 (including the active principle and the gelling agent):

|  | Prototype A | | Prototype B | | Prototype C | |
|---|---|---|---|---|---|---|
|  | Quantity (g) | Percentage composition* | Quantity (g) | Percentage composition* | Quantity (g) | Percentage composition* |
| Neutral cores | 750.0 g | 31.6% | 750.0 g | 30.0% | 750.0 g | 31.6% |
| Carbopol 971 ® | — | — | — | — | 375.0 g | 15.8% |
| Carbopol 974 ® | 375.0 g | 15.8% | 500.0 g | 20.0% | — | — |
| HPMC 603 | 250.0 g | 10.5% | 250.0 g | 10.0% | 250.0 g | 10.5% |
| Morphine sulphate | 750.0 g | 31.6% | 750.0 g | 30.0% | 750.0 g | 31.6% |
| Sustained release coating | 250.0 g | 10.5% | 250.0 g | 10.0% | 250.0 g | 10.5% |
| Total dry mass | 2375.0 g | 100.0% | 2500.0 g | 100.0% | 2375.0 g | 100.0% |

*Expressed in dry matter b) Preparation of the population 2 including the gelling activator: sodium bicarbonate The neutral cores used are sugar spheres (Neutrals #30 NPPHARM).

The size of these supports is of the order of 400 to 600 µm.

The binder agent used is polyoxyethyleneglycol 6000 (PEG 6000).

The gelling activator is sodium bicarbonate.

The PEG 6000, then sodium bicarbonate are solubilised in water, constituting the mounting solution. The mounting solution is sprayed in fluidised bed (Glatt), as is the coating suspension making it possible to avoid the sodium bicarbonate being released within she context of normal use.

Formulas of the different populations 2 (including the activator):

|  | Prototype A | | Prototype B | | Prototype C | |
|---|---|---|---|---|---|---|
|  | Quantity (g) | Percentage composition* | Quantity (g) | Percentage composition* | Quantity (g) | Percentage composition* |
| Neutral cores | 750.0 g | 25.0% | 750.0 g | 25.0% | 750.0 g | 25.0% |
| PEG 6000 | 750.0 g | 25.0% | 750.0 g | 25.0% | 750.0 g | 25.0% |
| Na bicarbonate | 750.0 g | 25.0% | 750.0 g | 25.0% | 750.0 g | 25.0% |
| Sustained release coating | 750.0 g | 25.0% | 750.0 g | 25.0% | 750.0 g | 25.0% |
| Total dry mass | 3000.0 g | 100.0% | 3000.0 g | 100.0% | 3000.0 g | 100.0% |

*Expressed in dry matter c) Mixture of the populations 1 and 2.

The populations 1 and 2 of each prototype A, B and C are then respectively mixed before encapsulation according to the following proportions:

|  | Prototype A | | Prototype B | | Prototype C | |
|---|---|---|---|---|---|---|
|  | Quantity (g) | Percentage composition* | Quantity (g) | Percentage composition* | Quantity (g) | Percentage composition* |
| Population 1 (with active principle) | 1900.0 g | 67.9% | 2000.0 g | 62.5% | 1900.0 g | 67.9% |
| Population 2 (with activator) | 900.0 g | 32.1% | 1200.0 g | 37.5% | 900.0 g | 32.1% |
| Total dry mass | 2800.0 g | 100.0% | 3200.0 g | 100.0% | 2800.0 g | 100.0% |

Example 1b: Sustained Release Usage Diversion-Resistant Microgranules of Morphine Sulphate a) Preparation, of the population 1, including the active principle and the gelling agent.

The active principle used is morphine sulphate.

The neutral cores used are sugar spheres (Neutrals #30 NPPHARM). The size of said supports is of the order of 400 to 600 μm.

The gelling agent used is an alginate derivative, type Protanal® 120 or 200.

The binder agent used is hydroxypropylmethylcellulose 603 (HPMC 603).

The Protanal® is solubilised in water, then the HPMC 603 and finally morphine sulphate are added to this aqueous solution, constituting the mounting solution. The mounting solution is sprayed in fluidised bed (Glatt), as is the coating suspension conferring the properties of sustained release to said population of microgranules.

Formulas of the different populations 1 (including the active principle and the gelling agent):

|  | Prototype A | | Prototype B | | Prototype C | |
| --- | --- | --- | --- | --- | --- | --- |
|  | Quantity (g) | Percentage composition* | Quantity (g) | Percentage composition* | Quantity (g) | Percentage composition* |
| Neutral cores | 750.0 g | 31.6% | 750.0 g | 31.6% | 750.0 g | 33.4% |
| Protanal | — | — | 375.0 g | 15.8% | 250.0 g | 11.1% |
| Protanal | 375.0 g | 15.8% | — | — | — | — |
| HPMC 603 | 250.0 g | 10.5% | 250.0 g | 10.5% | 250.0 g | 11.1% |
| Morphine sulphate | 750.0 g | 31.6% | 750.0 g | 31.6% | 750.0 g | 33.3% |
| Sustained release coating | 250.0 g | 10.5% | 250.0 g | 10.5% | 250.0 g | 11.1% |
| Total dry mass | 2375.0 g | 100.0% | 2375.0 g | 100.0% | 2250.0 g | 100.0% |

*Expressed in dry matter b) Preparation of the population 2 including the gelling activator: calcium chloride The neutral cores used are sugar spheres (Neutrals #30 NPPHARM). The size of said supports is of the order of 400 to 600 μm.

The binder agent used is polyoxyethyleneglycol 6000 (PEG 6000).

The activator is calcium chloride.

The PEG 6000, then calcium chloride are solubilised in water, constituting the mounting solution. The mounting solution is sprayed in fluidised bed (Glatt), as is the coating suspension making it possible to avoid the calcium chloride being released within the context of normal use.

Formulas of the different populations 2 (including the activator):

|  | Prototype A | | Prototype B | | Prototype C | |
| --- | --- | --- | --- | --- | --- | --- |
|  | Quantity (g) | Percentage composition* | Quantity (g) | Percentage composition* | Quantity (g) | Percentage composition* |
| Neutral cores | 750.0 g | 25.0% | 750.0 g | 25.0% | 750.0 g | 25.0% |
| PEG 6000 | 750.0 g | 25.0% | 750.0 g | 25.0% | 750.0 g | 25.0% |
| Calcium chloride | 750.0 g | 25.0% | 750.0 g | 25.0% | 750.0 g | 25.0% |
| Sustained release coating | 750.0 g | 25.0% | 750.0 g | 25.0% | 750.0 g | 25.0% |
| Total dry mass | 3000.0 g | 100.0% | 3000.0 g | 100.0% | 3000.0 g | 100.0% |

*Expressed in dry matter c) Mixture of populations 1 and 2

The populations 1 and 2 of each prototype A, B and C are then respectively mixed before encapsulation according to the following proportions:

|  | Prototype A | | Prototype B | | Prototype C | |
|---|---|---|---|---|---|---|
|  | Quantity (g) | Percentage composition* | Quantity (g) | Percentage composition* | Quantity (g) | Percentage composition* |
| Population 1 (with active principle) | 1900.0 g | 86.4% | 1900.0 g | 86.4% | 1800.0 g | 85.7% |
| Population 2 (with activator) | 300.0 g | 13.6% | 300.0 g | 13.6% | 300.0 g | 14.3% |
| Total dry mass | 2200.0 g | 100.0% | 2200.0 g | 100.0% | 2100.0 g | 100.0% |

Example 1c: Sustained Release Abuse-Deterrent Microgranules of Morphine Sulphate a) Preparation of the population 1, including the active principle and the gelling agent.

The active principle used is morphine sulphate.

The neutral cores used are sugar spheres (Neutrals #30 NPPHARM). The size of said supports is of the order of 400 to 600 μm.

The gelling agent used is a xanthan gum, type Vanzan®.

The binder agent used is hydroxypropylmethylcellulose 603 (HPMC 603).

The xanthan gum is solubilised in water, the HPMC 603 and finally morphine sulphate are added to this aqueous solution, constituting the mounting solution. TV-e mounting solution is sprayed in fluidised bed (Glatt), as is the coating suspension conferring the sustained release properties to said population of microgranules.

Formulas of the different populations 1 (including the active principle and the gelling agent):

|  | Prototype A | |
|---|---|---|
|  | Quantity (g) | Percentage composition * |
| Neutral cores | 750.0 g | 35.2% |
| Vanzan ® | 125.0 g | 5.9% |
| HPMC 603 | 250.0 g | 11.8% |
| Morphine sulphate | 750.0 g | 35.3% |
| Sustained release | 250.0 g | 11.8% |
| Total dry mass | 2125.0 g | 100.0% |

* Expressed in dry matter b) Preparation of the population 2 including she gelling activator: magnesium and aluminium silicate.

The neutral cores used are sugar spheres (Neutrals #30 NPPHARM). The size of said supports is of the order of 400 to 600 μm.

The binder agent used is polyoxyethyleneglycol 6000 (PEG 6000).

The activator is silicate of magnesium and aluminium.

The PEG 6000, then the silicate of magnesium and aluminium are dispersed in water, constituting the mounting suspension. The mounting suspension is sprayed in fluidised bed (Glatt), as is the coating suspension making it possible to avoid the silicate of magnesium and aluminium being released within the context of normal use.

Formulas of the population 2 (including the activator):

|  | Prototype A | |
|---|---|---|
|  | Quantity (g) | Percentage composition * |
| Neutral cores | 750.0 g | 20.0% |
| PEG 6000 | 750.0 g | 20.0% |
| Silicate of magnesium and aluminium | 1500.0 g | 40.0% |
| Sustained release coating | 750.0 g | 20.0% |
| Total dry mass | 3750.0 g | 100.0% |

* Expressed in dry matter c) Mixture of populations 1 and 2

The populations 1 and 2 are then respectively mixed before encapsulation according to the following proportions;

|  | Prototype A | |
|---|---|---|
|  | Quantity (g) | Percentage composition* |
| Population 1 (with active principle) | 1700.0 g | 68.0% |
| Population 2 (with activator) | 800.0 g | 32.0% |
| Total dry mass | 2500.0 g | 100.0% |

Example 2: Sustained Release Abuse-Deterrent Microtablets of Morphine Sulphate a) Preparation of the population 1

The population 1 including the active principle and the gelling agent.

The active principle used is morphine sulphate.

Into a mixer are introduced the active principle, macrocrystalline cellulose (Avicel PR102) and Protanal 120. A homogeneous mixture is obtained.

The mixer is stopped and magnesium stearate is added and the mixing operation is continued for 1 to 5 minutes depending on the mass of the mixture.

The tablet press is equipped with punches suited to the manufacture of microtablets and it is adjusted to obtain microtablets of mass of the order of 30 mg.

b) Preparation of the Population 2

The population 2 including the gelling activator. Into a mixer is introduced microcrystalline cellulose (Avicel PH102) and calcium, chloride. A homogeneous mixture is prepared.

The mixer is stopped and magnesium stearate is added and the mixing operation is continued for 1 to 5 minutes depending on the mass of the mixture.

The tablet press is equipped with dies adapted to the manufacture of microtablets and it is adjusted to obtain, microtablets of mass of the order of 30 mg.

Formulas of the Different Populations:

|  | % | g |
|---|---|---|
| Population 1 | | |
| Protanal 120 | 16.67% | 100.0 |
| Morphine | 33.33% | 200.0 |
| Avicel PH102 | 32.92% | 197.5 |
| Mg stearate | 0.42% | 2.5 |
| Sustained release coating | 16.67% | 100.0 |
| Total | 100.01% | 600.0 |
| Population 2 | | |
| Calcium | 41.67% | 250.0 |
| Avicel PH102 | 41.25% | 247.5 |
| Mg stearate | 0.42% | 2.5 |
| Sustained release coating | 16.67% | 100.0 |
| Total | 100.00% | 600.0 |

Suspension of Sustained Release Coating:

|  | Quantity |
|---|---|
| Eudragit L30D-55 | 63.33% |
| Talc | 12.5% |
| Triethyl citrate | 20.83% |
| Colloidal silica | 3.33% |
| Total dry mass | 100% |

The coating suspension conferring the properties of sustained release to said population of microtablets is sprayed in fluidised bed (Glatt).

b) Mixture of populations 1 and 2

The populations 1 and 2 are then respectively mixed before encapsulation according to the following proportions:

| Mixture | % | g |
|---|---|---|
| Population 1 | 71.43% | 600.0 |
| Population 2 | 28.57% | 240.0 |
| Total | 100.00 | 840.0 |

Example 3: Grinding Test of Microgranules Produced According to the Example 1a

|  | Population 1 | Population 2 |
|---|---|---|
| Neutrals | 60.00 mg | 40.00 mg |
| PEG6000 | | 40.00 mg |
| HPMC | 20.00 mg | |
| NaHC03 | | 40.00 mg |
| Carbopol 974 | 40.00 mg | |
| Carbopol 971 | | |
| e.g.: Morphine | 60.00 mg | |
| Sustained release coating | 20.00 mg | |
| Total | 200.00 mg | 120.00 mg |
| Total for 1 capsule | | 320.00 mg |

The microgranules of a capsule are crushed then thinned down in 1 ml of water. The resulting solution is a compact gel unsuitable for injection IV.

When the same experiment is repeated, with 2, 5 or 10 ml, the resulting solution is a viscous gel unsuitable for injection IV.

Example 4: The Example 2 was Reiterated with the Following 4 Formulations

Example 4a

|  | weighing (g) | mg/cp | % |
|---|---|---|---|
| Population 1 | | | |
| HCl Hydromorphone | 64.00 | 4.80 | 16.0 |
| Carbopol 71G | 111.30 | 8.35 | 27.8 |
| Kolidon SR | 222.10 | 16.70 | 55.7 |
| Mg stearate | 2.00 | 0.15 | 0.5 |
| Total | 400.00 | 30.00 | 100.0 |
| Population 2 | | | |
| Sodium bicarbonate | 160.00 | 12.00 | 40.0 |
| Avicel pH200 | 236.00 | 17.70 | 59.0 |
| Syloid | 2.00 | 0.15 | 0.5 |
| Mg stearate | 2.00 | 0.15 | 0.5 |
| Total | 400.00 | 30.0 | 100.0 |

The final dosage form, for this example is a mixture of microtablets of the populations 1 and 2 with for example the following ratio: 5 microtablets of the population 1 and 4 microtablets of the population 2. This corresponds to a dose of 24 mg of hydromorphone HCl per dosage unit. The quantity of gelling agent (Carbopol 71 G) is 42 mg and that of gelling activator (sodium bicarbonate) is 48 mg. Said mixture of microtablets may be conditioned in capsules or in single dose packaging.

Example 4b

| Population 1 | weighing (g) | mg/cp | % |
|---|---|---|---|
| HCl Hydromorphone | 64.00 | 4.80 | 16.0 |
| Protanal LF 200 | 111.30 | 8.35 | 27.8 |

-continued

|  | weighing (g) | mg/cp | % |
|---|---|---|---|
| Kolidon SR | 222.70 | 16.70 | 55.7 |
| Mg stearate | 2.00 | 0.15 | 0.5 |
| Total | 400.00 | 30.00 | 100.0 |
| Population 2 | weighing (g) | mg/cmp | % |
| Calcium chloride | 160.00 | 12.00 | 40.0 |
| Avicel pH200 | 236.00 | 17.70 | 59.0 |
| Syloid | 2.00 | 0.15 | 0.5 |
| Mg stearate | 2.00 | 0.15 | 0.5 |
| Total | 400.00 | 30.00 | 100.0 |

The final dosage form for this example is a mixture of the microtablets of populations 1 and 2 with for example the following ratio: 7 microtablets of the population 1 and 1 microtablets of the population 2. This corresponds to a dose of 34 mg of hydromorphone HCl per dosage unit. The quantity of gelling agent (Protanal LF 200) is SS mg and that of gelling activator (calcium chloride) is 12 mg. This mixture of microtablets may be conditioned in capsules or in single dose packaging.

Example 4c

|  | weighing (g) | mg/cp | % |
|---|---|---|---|
| Population 1 |  |  |  |
| Oxycodone HCI | 64.00 | 4.80 | 16.0 |
| Carbopol 71G | 111.30 | 8.35 | 27.8 |
| Avicel PH200 | 222.70 | 16.70 | 55.7 |
| Mg stearate | 2.00 | 0.15 | 0.5 |
| Total | 400.00 | 30.00 | 100.0 |
| Population 2 |  |  |  |
| Sodium bicarbonate | 160.00 | 12.00 | 40.0 |
| Avicel PH200 | 236.00 | 17.70 | 59.0 |
| Syloid | 2.00 | 0.15 | 0.5 |
| Mg stearate | 2.00 | 0.15 | 0.5 |
| Total | 400.00 | 30.00 | 100.0 |

The final dosage form for this example is a mixture of the microtablets of populations 1 and 2 with for example the following ratio: 9 microtablets of the population 1 and 8 microtablets of the population 2. This corresponds to a dose of 43 mg of oxycodone HCl per dosage unit. The quantity of gelling agent (Carbopol 71 G) is 75 mg and that of gelling activator (sodium bicarbonate) is 96 mg. Said mixture of microtablets may be conditioned in single dose packaging or in sachets.

Example 4d

|  | weighing (g) | mg/cp | % |
|---|---|---|---|
| Population 1 |  |  |  |
| Oxycodone HCI | 64.00 | 4.80 | 16.0 |
| Xanthan gum | 111.30 | 8.35 | 27.8 |
| Kolidon SR | 222.70 | 16.70 | 55.7 |
| Mg stearate | 2.00 | 0.15 | 0.5 |
| Total | 400.00 | 30.00 | 100.0 |

-continued

| Population 2 | weighing (g) | mg/cp | Quantity (%) |
|---|---|---|---|
| Veegum NF-F | 160.00 | 12.00 | 40.0 |
| Syloid 244 | 4.00 | 0.30 | 1.0 |
| Avicel Ph200 | 234.00 | 17.55 | 58.5 |
| Mg stearate | 2.00 | 0.15 | 0.5 |
| Total | 400.00 | 30.00 | 100.0 |

The final dosage form for this example is a mixture of the microtablets of populations 1 and 2 with for example the following ratio: 2 microtablets of the population 1 and 8 microtablets of the population 2. This corresponds to a dose of 9.6 mg of oxycodone HCl per dosage unit. The quantity of gelling agent (Xanthan gum) is 16.7 mg and that of gelling activator (Veegum NF-F) is 96 mg. Said mixture of microtablets may be conditioned in single dose packaging or in sachets.

Example 5: Extraction Tests Carried Out on the Dosage Forms of Examples 4

The method used is the following: the micro-tablets of the final dosage form are ground for 2 minutes in a mortar using a pestle in order to reduce them into a fine powder. Said powder is then transferred into 20 mL beakers in which is placed a magnetic bar, 10 mL of the different solvents are added and stirred for exactly 5 minutes. Then the samples are filtered on filter paper in a glass tube for exactly 1 h. If no filtrate has passed, the sample is filtered using a syringe equipped with a glass fibre filter of 1 μm (GF/B). The filtrate obtained is diluted to $\frac{1}{10}$th in 0.1 N HCl. In the case where no filtrate, is obtained, it is concluded that 0% of the active principle was able to be extracted. Finally, the samples are passed in HPLC with the aim of determining the percentage of active principle extracted.

Concerning Oxycodone HCl, the HPLC analysis is carried out with a C18 column in inverse phase with UV detection at 280 nm. The elution solvent is a mixture of water, heptanesulphonic acid and acetonitrile.

Concerning Hydromorphone HCl, the HPLC analysis is carried out with a C18 column in phase inverse with UV detection at 230 nm. The elution solvent is a mixture of water, heptanesulphonic acid and acetonitrile.

The tables below group together the extraction of the different formulations of examples 4.

The percentages presented correspond to the percentage of active principle passed in the filtrate after grinding and extraction in the different solvents tested. This corresponds to the percentage of the initial dose contained in the dosage form that a person wishing to divert it could inject.

In the left hand column of each table is presented the % recoverable when only the microtablets with active principle and gelling agent (population 1) are used for the extraction. In the right hand column, to the population 1 are added the microtablets of the population 2. The quantities used to carry out these tests are those presented in the example 4.

The interest of testing in parallel with and without the population 2 makes it possible to demonstrate its interest within the scope of the present invention.

Example 5a: Results Obtained with the Final Dosage Form of the Example 4a

| Gelling agent | Carbopol (42 mg) | |
|---|---|---|
| Gelling activator | — | Na bicarbonate (48 mg) |
| Active principle | Hydromorphone (24 mg) progressive release | |
| Solvent | % recovered | % recovered |
| Water | 33.3% | 0.0% |
| Water + 40% EtOH | 25.4% | 6.7% |

Example 5b: Results Obtained with the Final Dosage Form of the Example 4b

| Gelling agent | Protanal (58 mg) | |
|---|---|---|
| Gelling activator | — | CaCl2 (12 mg) |
| Active principle | Hydromorphone (34 mg) | |
| Solvent | % recovered | % recovered |
| Water | 29.1% | 0.0% |
| Water + 40% EtOH | 29.1% | 17.2% |

Example 5c: Results Obtained with the Final Dosage Form of the Example 4c

| Gelling agent | Carbopol (75 mg) | |
|---|---|---|
| Gelling activator | — | Na bicarbonate (96 mg) |
| Active principle | Oxycodone (43 mg) immediate release | |
| Solvent | % recovered | % recovered |
| Water | 37.2% | 0.0% |
| 0.1N HCl | 19.6% | 16.0% |

Example 5d: Results Obtained with the Final Dosage Form of the Example 4d

| Gelling agent | Xanthan gum (16.7 mg) | |
|---|---|---|
| Gelling activator | — | Veegum (96 mg) |
| Active principle | Oxycodone (9.6 mg) | |
| Solvent | % recovered | % recovered |
| Water | 0.0% | 0.0% |
| Water + 40% EtOH | 0.0% | 0.0% |
| Ethanol | 57.2% | 11.4% |
| 0.1N HCl | 15.9% | 0.7% |
| Kitchen vinegar | 7.3% | 0.5% |

Example 6: Dissolution Tests Carried Out on the Dosage Forms of Examples 4

With the aim of showing that different types of release profiles may be envisaged, dissolution tests were carried out on the different formulas of examples 4, on the non-crushed microtablets.

The dissolution conditions are the following:

For the active principle hydromorphone HCl, the dissolution tests were carried out in a dissolution bath according to the European pharmacopoeia, the stirrers of each vessel being equipped with, blades turning at 100 rpm. The dissolution medium used is 0.5 composed of 500 ml, of pH 6.8 buffer at 37° C. The analysis of the different points of dissolution being carried out by HPLC at 230 nm according to the method described in the example 5.

For the active principle oxycodone HCl, the dissolution, tests were carried out in a dissolution bath according to the European Pharmacopoeia, the stirrers of each vessel being equipped with, baskets turning at 100 rpm. The dissolution medium used is composed of 900 mL of pH 1.2 buffer at 37° C. The analysis of the different points of dissolution being carried out by HPLC at 230 nm according to the method described in the example 5.

The results obtained are presented in FIG. 1. The dissolution profiles are different from each other, showing that despite an intense gelling when the form is diverted, when the tablets are intact, it is possible to obtain more or less rapid release profiles.

The invention claimed is:

1. An oral dosage form based on microgranules and/or microtablets comprising two populations of microgranules or microtablets, the first population comprising at least one active principle that could create a dependency and a gelling agent, and the second population, without active principle and gelling agent, comprising at least one gelling activator, wherein the first population contains no gelling activator, and wherein the two populations have an identical external appearance.

2. The dosage form according to claim 1, consisting of microgranules or microtablets.

3. The dosage form according to claim 2, comprising a first population of microgranules comprising a neutral support and at least one mounting layer comprising the at least one active principle and optionally a pharmaceutically acceptable binder agent, said gelling agent being present either in the mounting layer or in a separate layer, and a second population of microgranules comprising a neutral support and at least one mounting layer comprising the at least one gelling activator.

4. The dosage form according to claim 1, wherein the gelling agents are chosen from polyacrylic acids and derivatives thereof, polyoxyethylenes, polyvinyl alcohols, polyvinylpyrrolidones (PVP), gelatines, derivatives of cellulose, polysaccharides, and mixtures thereof.

5. The dosage form according to claim 1, wherein the gelling activator, in association with the gelling agent, enables the formation of bridges at certain sites of the polymeric chains of the gelling agent or/and enables the reinforcement of the polymeric network of the gelling agent.

6. The dosage form according to claim 1, wherein, the gelling agent/gelling activator pair is chosen from carboxy polymethylene/sodium bicarbonate, alginate/$Ca^{2+}$ ion, alginate/magnesium and aluminium silicates and xanthan gum/magnesium and aluminium silicates.

7. The dosage form according to claim 1, wherein the gelling agent is present in the dosage unit at a rate of 1 to 100 mg.

8. The dosage form according to claim 1, wherein the gelling activator is present in the dosage unit at a rate of 1 to 100 mg.

9. The dosage form according to claim 1, wherein the microgranules and/or the microtablets comprise a coating based on at least one hydrophobic polymer to prevent the immediate release of the active principle.

10. The dosage form according to claim 9, wherein the hydrophobic polymer is chosen from ethylcellulose, cellulose butyrate acetate, cellulose acetate, type A and type B ammonio-methacrylate copolymers of the family of poly (ethyl acrylate, methyl methacrylate, trimethylamonioethyl methacrylate), polyvinylacetates and mixtures thereof.

11. The dosage form according to claim 10, wherein the coating comprises at least one plastifier.

12. The dosage form according to claim 1, wherein the active principle is chosen from analgesics and particularly non opiate, low opiate analgesics, mixed opioids, morphinics or spasmodics, particularly hydrocodone, hydromorphone, morphine, oxycodone, oxymorphone, tramadol and derivatives thereof.

13. The dosage form according to claim 1, wherein the microgranules or the microtablets are conditioned in capsule form.

14. The dosage form according to claim 1, wherein the microgranules or the microtablets are conditioned in multiparticulate tablet form.

15. The dosage form according to claim 1, wherein the microgranules or the microtablets are conditioned in single dose packaging.

* * * * *